United States Patent [19]

Heflin

[11] Patent Number: 4,628,523
[45] Date of Patent: Dec. 9, 1986

[54] DIRECTION CONTROL FOR RADIOGRAPHIC THERAPY APPARATUS

[75] Inventor: Chester L. Heflin, San Jose, Calif.

[73] Assignee: B.V. Optische Industrie de Oude Delft, Netherlands

[21] Appl. No.: 733,196

[22] Filed: May 13, 1985

[51] Int. Cl.⁴ .................. H05G 1/02; A61B 6/08; H01J 29/02
[52] U.S. Cl. .................... 378/193; 378/196; 378/205; 250/522.1
[58] Field of Search ............... 378/193, 196, 197, 205, 378/206, 65, 195, 198, 208, 209, 20; 250/522.1

[56] References Cited

U.S. PATENT DOCUMENTS

| | | | |
|---|---|---|---|
| 2,781,454 | 2/1957 | Green et al. | 250/91 |
| 3,420,997 | 1/1969 | Mueller | 250/57 |
| 3,708,664 | 1/1973 | Bock et al. | 250/61.5 |
| 3,783,251 | 1/1974 | Pavkovich | 235/151 |
| 4,118,631 | 10/1978 | Froggatt | 250/492 |
| 4,132,900 | 1/1979 | Smith et al. | 250/491 |
| 4,139,776 | 2/1979 | Hellstrom | 250/445 |
| 4,426,725 | 1/1984 | Grady | 378/196 |

Primary Examiner—Craig E. Church
Assistant Examiner—Charles Wieland
Attorney, Agent, or Firm—Gausewitz, Carr & Rothenberg

[57] ABSTRACT

An X-ray simulator has an X-ray source and collimator connected to the end of a cantilevered horizontal arm mounted on a gantry that rotates about a horizontal axis and extends along a patient supporting table. The horizontal arm has an asymmetrical cross section that causes the arm and therefore the X-ray source and collimator to deflect by differing amounts as the gantry rotates. To compensate for the varying displacement of the X-ray target point and to adjust the position of the target point along the rotation axis of the gantry, the collimator is pivoted in one direction or the other in accordance with the amount of rotation of the gantry axis.

13 Claims, 6 Drawing Figures

DIRECTION CONTROL FOR RADIOGRAPHIC THERAPY APPARATUS

BACKGROUND OF THE INVENTION

A radio treatment thereby simulator is employed to improve efficiency and accuracy of radio therapy planning, allowing more precise tumor localization and assessment of target volume. It enables exact simulation of the actual treatment plan. The X-ray simulator comprises a patient couch positioned between the horizontally extending arms of a C-shaped gantry that is mounted for rotation about a horizontal axis extending substantially along the patient supporting couch. An X-ray source and collimator on the end of one arm cooperate with a film holder on the other arm to enable X-ray and fluoroscopic analysis and study of the patient. The collimator includes a reticle having a set of cross hairs, the intersection of which forms a target point that is projected onto the patient's body substantially at the X-ray beam axis. The projection of the target point enables precisely located marks to be made upon the patient's body for use in analysis and assessment of tumor location and subsequent treatment. Precision of the actual treatment depends in part upon target point location. However, precision location of the target point formed by the collimator assembly cross hairs is difficult to achieve and subject to many errors which may include bending of the cantilevered support arm, tolerance in the mounting of the support arm or the gantry, and tolerance in mounting of the X-ray head itself to the support arm. A major error source is deflection of the support arm which, because it is generally constructed with an asymmetrical cross section, experiences different amounts of deflection at different positions of gantry rotation.

Errors in the positioning of the target point are minimized by manufacture of the gantry and support arm by making the structure sufficiently massive and rigid to bring the aiming errors caused by arm deflection and the like down to an acceptable level. Thus, in one high quality X-ray simulator, the isocentric accuracy, that is the location of the target point on or along the rotation (isocentric) axis in various positions of gantry rotation, has a tolerance of one millimeter in a direction transverse to the isocentric axis and of two millimeters in a direction along the isocentric axis. Nevertheless, if the length or weight of the arm should be increased as, for example, by employing an X-ray head or adjustable mounting that provides weight greater than design weight at the end of the support arm, deviation of the target point along the isocentric axis may be increased beyond acceptable limits. Accordingly, it is an object of the present invention to provide apparatus in which target point tolerances are significantly decreased.

SUMMARY OF THE INVENTION

In carrying out principles of the present invention in accordance with a preferred embodiment thereof, an energy beam source carried by a support arm that extends along and is spaced from part of a patient supporting table is adjustably mounted to the support arm to enable shifting of the energy beam source so as to decrease displacement between the projected target point and the machine isocenter. In a specific embodiment, the collimator assembly, which includes a pair of target point defining cross hairs is pivoted to the X-ray head and pivotally shifted in one direction or the other by an amount related to the rotational position of the machine gantry.

DETAILED DESCRIPTION

Figure 1:
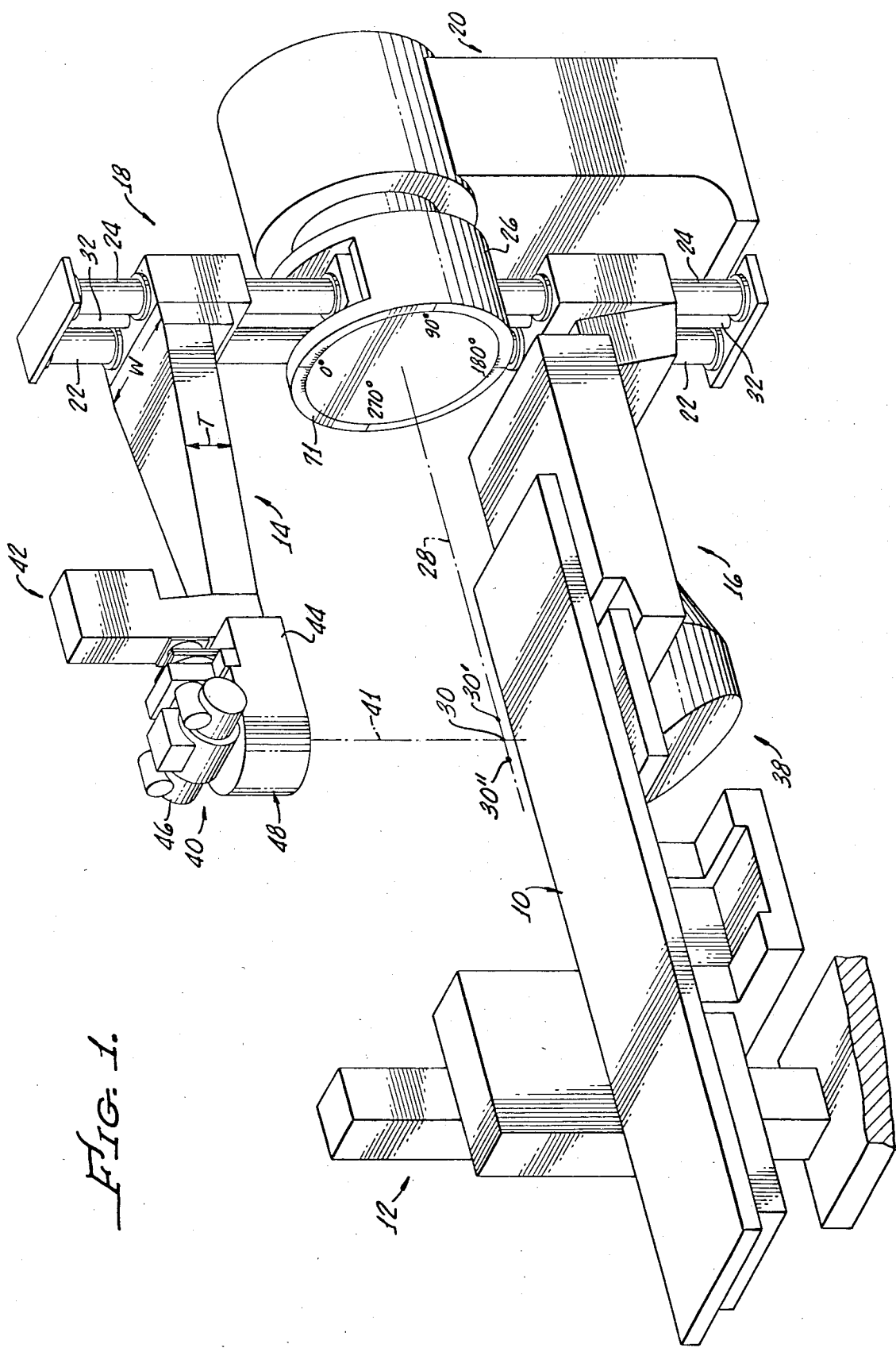
FIG. 1 is a pictorial view of an X-ray simulator embodying principles of the present invention.

As illustrated in FIG. 1, an X-ray simulator includes a patient supporting table or couch 10 adjustably carried upon a fixed floor supported column 12 and, in the position illustrated, extending horizontally between upper and lower arms 14,16 of a substantially C-shaped gantry 18 carried upon a fixed floor mounted gantry column 20. The gantry comprises twin parallel mutually spaced tubes 22,24 fixed to a hub 26 that is rotatably mounted to column 20 for rotation about a horizontal rotation or isocentric axis 28 that extends through the machine isocenter 30. The machine isocenter is an aiming point on the axis of rotation of the gantry at which a projected target point is to be directed. Arm 16 is slidably and guideably mounted on the lower ends of the twin tubes 22,24 and may be driven along the tubes to different adjustable positions by means of a motor driven screw 32. Arm 16, which is cantilevered from the twin tubes, carries at its free end apparatus such as an X-ray film holder or fluoroscopic device 38. Upper arm 14 is also slidably and guideably mounted upon the twin tubes 22,24 at the other side of hub 26 and is also longitudinally driven along the tubes by the screw 32. The drives for arms 14,16 may be arranged to move the arms independently or simultaneously along the tubes. Partly because of the requirement for adjustable positioning of the arm 14, the arm has a relatively smaller dimension T in the direction of the axis of the twin tubes 22,24. To maximize rigidity, the arm has a relatively larger dimension W in its width, which is its transverse horizontal dimension in the position illustrated in FIG. 1. An energy beam source in the form of an X-ray head 40 is carried at the outer end of the cantilevered arm 14. Frequently the X-ray simulator is manufactured with the X-ray head 40 directly secured to the free end of the arm 14. However, if additional vertical travel is necessary, the arm may be modified by adding an additional vertical adjusting mechanism at the end of the arm. In order to provide such increased travel of the X-ray head 40 in a direction parallel to the axes of the tubes 22,24, the free end of arm 14 is provided with a fixed upstanding elevator housing 42 to which the X-ray head 40 is mounted for sliding motion (vertically in the gantry position of FIG. 1) under control of a motor (not shown). The X-ray head includes a support structure 44 fixedly carrying an X-ray tube 46 and a collimator assembly 48, all of which are adjustable as a unit along the vertical length of elevator housing 42.

Figure 4:
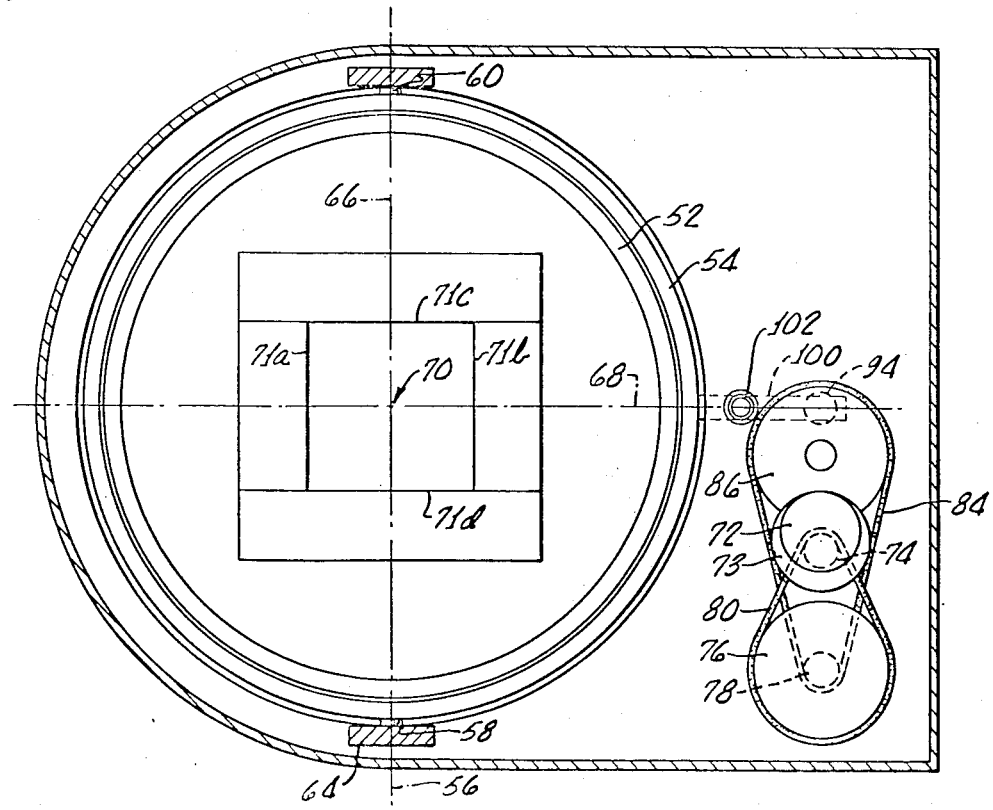
FIG. 4 is a horizontal section showing the pivotal mounting of the collimator assembly.
Figure 3:
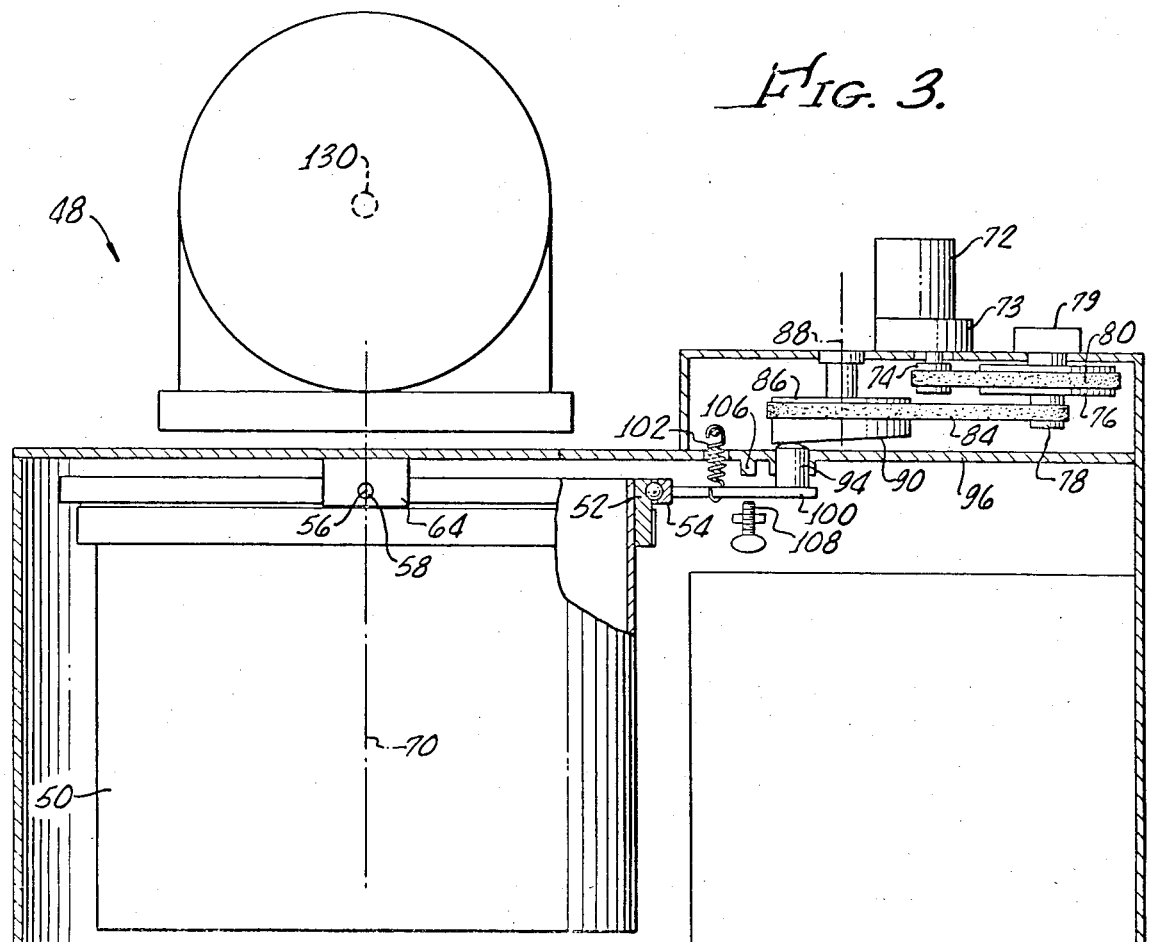
FIG. 3 is a side elevational view of the collimator assembly adjusting mechanism.

The collimator assembly as illustrated in FIGS. 3 and 4 includes a collimator housing 50 which carries an inner bearing ring 52 rotatably mounted within an outer bearing ring 54 to enable the collimator housing to be rotated about a vertical axis (e.g., an axis substantially parallel to the axes of tubes 22,24). Outer bearing ring 54 is mounted for limited pivotal motion about a pivot axis 56 by means of a pair of diametrically opposed pivot pins 58,60 which are carried by a fixed collimator support 64 which in turn is fixedly mounted to the fixed head structure 44.

The collimator housing carries a recticle having a pair of cross hairs 66,68 which intersect at a target point 70. The cross hairs are substantially centered on the axis of the X-ray beam projected by the X-ray head and thus cast a shadow of target point 70 on a patient supported on the table. The collimator assembly may additionally include shiftable diaphragm plates (not shown) which are adjustable to control the area of the projected X-ray field and two pairs of field defining wires 71a, b, c and d (FIG. 4) which may be adjusted to cast a rectangular shadow of adjustably varying dimensions precisely centered upon the cross hair target point.

The X-ray beam is projected along an axis 41 and directed substantially at the machine isocenter 30, which is a point on isocentric axis 28. Ideally the collimator assembly is positioned so that the projected target point will fall precisely at the machine isocenter 30. However, in the position illustrated, with the smaller dimension T of the arm 14 vertical, the asymmetrical arm 14 deflects by a maximum amount and shifts the target point inwardly along the isocentric axis to a point 30' (FIG. 1). The amount of this displacement is increased by the added weight of the vertical housing 42 together with the related structure and motor required for the augmented travel of the energy beam head 40. Further, additional tolerances in the movable mounting of the head to the vertical housing 42 also tend to increase the inward (toward the gantry support) displacement of the projected target point on the machine rotation axis. The displacement of the target point from the isocenter 30 to a point such as point 30' may be sufficiently small, in the absence of the structure including column 42 that has been added to increase the vertical travel of the machine. However, when this additional structure and weight are imposed upon the end of the beam arm 14, the displacement of the target point is increased to a degree that is no longer acceptable in some applications.

The apparatus, as illustrated in FIG. 1, is in a 0° position of rotation, as indicated by a circular scale 71 on the face of hub 26. The entire gantry including twin tubes 22,24 and both arms 14 and 16, is rotatable about the machine axis 28 through nearly 180° in either direction thereby providing a nearly full 360° of rotational motion. With the gantry rotated through 90° to either the 90° or 270° position, the larger dimension W of arm 14 becomes vertical and, therefore, in this position the arm experiences a minimum amount of deflection. As rotation continues beyond the 90° or 270° position toward the 180° or 360° position, deflection of arm 14 begins to increase, but this deflection is in the opposite direction as compared to the deflection occurring with the arm in 0° position. Thus, with the gantry near its 180° position, the X-ray head is substantially underneath the patient table 10 with the film holder apparatus 38 positioned above the patient and table. Accordingly, in this position deflection of the gantry arm 14 is such as to displace the target point in the opposite direction from the isocenter 30, to a point such a point 30'' that is further displaced from the gantry hub (as indicated in the schematic illustration of FIG. 6). Thus, in rotating from 0° to a 90° position, displacement of the target point decreases from a maximum to a minimum and then upon continued rotation from the 90° to a 180° position, displacement of the target point again increases but in the opposite direction to its opposite maximum value. The same is true for rotation in the other direction from the 0° position to the 270° position and then continuing on to the 360° position.

In order to compensate for this varying displacement of the projected target point relative to the machine isocenter, the energy beam source or more specifically the collimator assembly, which is part of the energy beam source, is slightly pivoted in one direction or the other about pivot axis 56 in accordance with the rotational position of the gantry. Axis 56 is substantially perpendicular to a plane containing the isocentric axis 28 and a point at or near the center of the X-ray source, such plane also containing the X-ray beam axis. To accomplish this compensation, a compensation motor 72, FIG. 3, is fixedly mounted upon the head structure 44 and connected via a gear box 73, pulleys 74, 76 and 78 and belts 80,84 to drive a cam disc 86 that is mounted to the fixed head structure 44 for rotation about an axis 88, which is perpendicular to both pivot axis 56 and isocentric axis 28. An angular position pickoff potentiometer 79 is driven by pulley 78. Cam disc 86 has a downwardly (in the gantry position shown in FIG. 3) facing flat inclined cam surface 90 that is cut at a selected small angle to its rotational axis 88 so that the cam surface 90 tapers uniformly from an area of minimum thickness at one point at the periphery of the surface to an area of maximum thickness at a diametrically opposite point of the cam surface. The cam is mounted so as to be substantially completely restrained against axial motion. A cam follower 94 is slidably mounted in an apertured plate 96 of the fixed structure 44 and has its upper end bearing against the cam surface 90. The lower end of the cam follower rests upon a flattened surface of a cylindrical rod 100 that is fixedly connected to the outer bearing ring 54 at a point on the ring midway between the pivot pins 58,60. Rod 100, which extends substantially along a radius of the ring 54 in a direction perpendicular to the pivot axis 56, is urged upwardly by means of a tension spring 102 that is secured at one end to rod 100 and at the other end to the fixed structure 44 above the rod. A stop 106 is mounted to structure 44 and spaced slightly above arm 100 while a screw 108 is axially adjustable to provide an adjustable stop for the opposite side of the rod 100, whereby motion of the rod is limited to a small distance between the fixed stop 106 and the end of adjusting screw 108.

Figure 5:
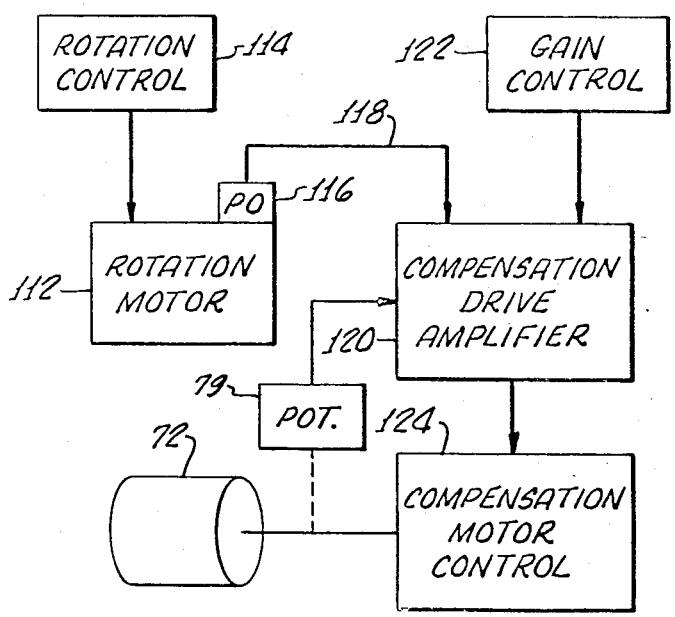
FIG. 5 is a simplified functional block diagram of the control arrangement for the pivotal collimator assembly.

As shown in FIG. 5, a rotation motor 112 that rotates the gantry 18 about the rotation axis 28 is driven from a rotation control 114. A rotation angle pickoff 116, associated with the motor or the elements rotated thereby, provides an output signal on a line 118 representing the rotational position of the gantry. The signal on line 118 is fed to a compensation drive amplifier 120 having an adjustable gain control 122. From the amplifier a position control signal is fed to a compensation motor control servo 124 having an output that drives the compensation motor 72. The position control signal from the amplifier circuit 120 is proportional to the difference between the gantry rotation signal on line 118 and the compensation motor position feedback signal from potentiometer 79. The arrangement in effect slaves the rotational position of cam 86 to the rotational position of the gantry 18.

As the cam 86 rotates, cam follower 94 moves along the inclined surface 90 between positions of minimum and maximum thickness. As the cam follower moves towards a position of maximum thickness, the rod 100 is forced downwardly (in the orientation of FIG. 3) to thereby pivot the collimator assembly in a clockwise direction (as viewed in FIG. 3). As the cam follower moves along the cam surface from a position of greater to a position of lesser thickness, the rod 100 is pulled upwardly by spring 102 to thereby pivot the collimator assembly in a counterclockwise direction (as viewed in FIG. 3). The total amount of pivotal motion of exceedingly small and may be considerably less than one half degree. Displacement of the target point on the patient is amplified by the relatively large distance between the pivot point and the isocentric axis and, moreover, the actual amount of error due to arm deflection is relatively small, in the order of several millimeters.

Figure 6:
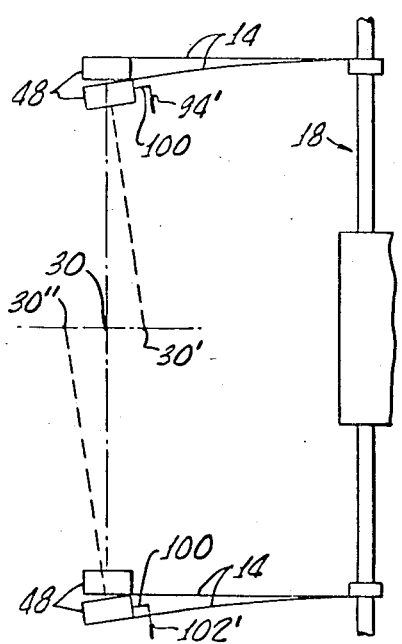
FIG. 6 is a schematic illustration of the gantry in two opposite positions, showing the direction of target point displacement, greatly exaggerated.

The dimensions of parts and cam surface inclination are chosen to provide the desired minimum and maximum amount of target point displacement compensation at the various rotational positions of the gantry. Thus, with the gantry in its 90° position with the twin tubes 22,24 substantially horizontal deflection of the arm 14 is at its minimum and the cam and cam follower structure are arranged so that cam follower 94 engages the cam surface at a point half way between the minimum and maximum thickness of the cam. As the gantry rotates from the 90° position to the 0° position, displacement of the target point increases, moving toward point 30' (FIGS. 1 and 6). Accordingly, the cam follower moves along the cam surface toward the cam area of maximum thickness. This movement of the cam follower forces arm 100 downwardly and causes a clockwise pivotal motion of the collimator assembly which in turn causes the target point to move outwardly along the rotation axis 28, toward the isocenter 30.

Figure 2:
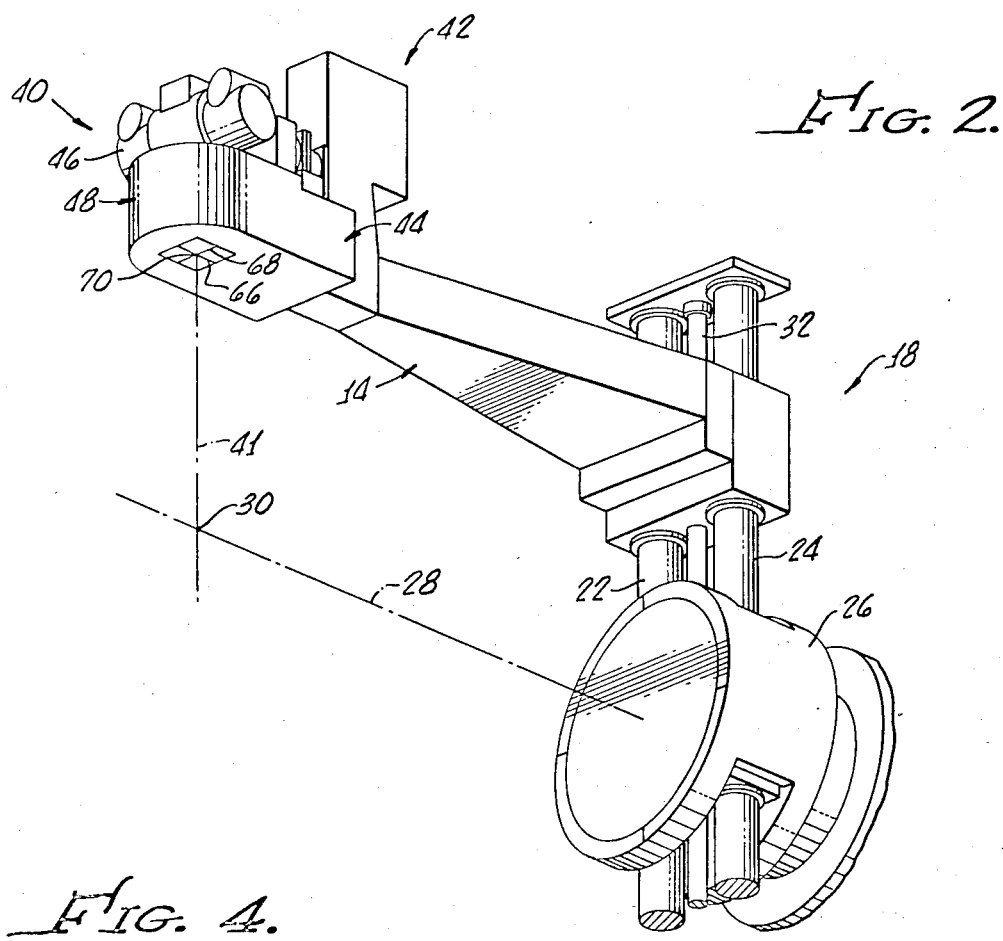
FIG. 2 is a pictorial view of the X-ray head showing the reticle of the collimator assembly.

Similarly, with the machine gantry in its 90° position, further clockwise rotation (as viewed from the patient platform) of the gantry toward the 180° position causes deflection of arm 14 downwardly (see FIG. 6) to effect displacement of the target point in the opposite direction, toward the displaced point 30''. In the course of this motion of the gantry from the 90° to 180° position the slaved rotation of the cam causes the cam follower to move from a point of intermediate cam thickness toward a point of minimum cam thickness, allowing spring 102 to pull on rod 100 and pivot collimator assembly 50 (which is now substantially upside down) in the opposite direction to shift the target point inwardly, back toward the isocenter point 30. Thus, with the gantry in its 0° position as illustrated in FIGS. 1 and 2, the cam follower 94 engages an area of the cam of greater thickness and thus pushes down upon rod 100 to swing the inner or lower end of the collimator housing assembly away from the gantry hub. This action of the cam follower is represented by arrow 94' in FIG. 6, to show the direction of force exerted on rod 100. Of course, deflections shown in FIG. 6 are greatly exaggerated. With the gantry in its opposite 180° position the cam follower engages the cam surface at a point of lesser thickness, allowing the spring to act upon the rod, pulling down upon the rod (with the head in its upside down position) to swing the free or now upper end of the collimator assembly inwardly, toward the machine hub assembly, to thereby move the target point inwardly toward the isocenter. This action of spring 102 is represented by arrow 102' in FIG. 6 to show the direction of force exerted on the rod in the 180° position. Thus, with the machine gantry in a position between the 0° and 90° position, the collimator assembly is pivoted in one direction whereas with the gantry in a position between 90° and 180° the collimator assembly is pivoted in the opposite direction. A similar analysis applies to gantry positions between 0° and 270° and between 270° and 360° where the 270° position is analogous to the 90° position, where arm 14 is in its position of minimum deflection. Thus, it will be seen that deflection of arm 14 varies from a minimum at 90° to maxima at 0° and 180° of gantry rotation, and the cam, which rotates in accordance with gantry position, causes a compensatory pivoting of the collimator assembly that is proportional to the target point deviation and in the proper direction.

The amount of collimator pivoting caused by an increment of gantry rotation is readily controllable by adjustment of the compensation motor servo system. Thus, by decreasing the gain of the compensation drive amplifier a smaller amount of collimator assembly pivoting will be commanded by a given amount of gantry rotation and vice versa. The parts are arranged so that, at maximum and minimum beam deflections, the cam follower contacts the cam surface short of the points of maximum and minimum cam thickness. This allows either increase or decrease of amplifier gain.

It will be readily observed that the described arrangement not only will compensate for added amount of deflection caused by increased weight of the auxiliary elevation adjustment mechanism added to the end of arm 14, but may also be employed to still further decrease target point deviation from isocenter and to compensate for deflection caused by the weight of the basic arm structure 14 itself. Thus, the arrangement of the present invention as described herein enables decrease of deviation of the target point to provide an aiming precision considerably greater than presently available with the existing machines. Conversely, principles of the invention may allow use of an arm structure that is less rigid but without loss of aiming precision.

In an alternative arrangement the cam and cam follower drive for rod 100 can be replaced by a weight of appropriate mass secured to the free end of the rod. This would tend to pivot the collimator assembly in one direction or the other and in an amount according to the angle of gantry rotation. However, such an arrangement provides less positive control of pivotal position of the collimator assembly and does not provide for as simple and ready adjustment of system gain as the earlier described arrangement.

Ideally, the pivoted compensation, as described above, employs pivotal motion of the entire energy source head including the X-ray tube and the collimator assembly, about an axis 130 (FIG. 3) extending through the center of the energy beam source. However, existing structural constraints involved in the mounting of the energy beam source, the X-ray tube and the collimator assembly enable the described mechanization (with the collimator assembly pivoted to a fixed bearing ring on axis 56) to be implemented with a minimum degree of structural redesign and modification. For purposes of this apparatus the pivotal mounting of the collimator assembly, is the effective equivalent of a pivotal mounting of the energy beam source.

Although principles of the invention have been described in connection with an X-ray simulator in which the invention has been initially embodied, it will be readily appreciated that these concepts may be equally applied to different types of radiographic and radio therapy apparatus in which an energy beam source is carried by a support that is subject to deflection which causes undesired displacement of the projected beam axis.

The foregoing detailed description is to be clearly understood as given by way of illustration and example only, the spirit and scope of this invention being limited solely by the appended claims.

What is claimed is:

1. Radiant energy apparatus comprising:
   a patient supporting table,
   a machine support,
   an energy beam source,
   a support arm carried by said machine support,
   said arm extending along and spaced from a portion of said table, and
   means for mounting said energy beam source to said support arm to enable said energy beam source to project a target point along an energy beam axis toward an isocenter point having a predetermined position with respect to said machine support, said means for mounting comprising adjustable means for automatically adjusting the direction of said energy beam axis relative to said support arm to decrease displacement between said projected target point and said isocenter point, said support arm being mounted to said machine support for rotation about a rotation axis extending through said isocenter point, and said adjustable means comprising means for adjusting the direction of said energy beam axis by an amount related to rotation of said support arm.

2. The apparatus of claim 1 wherein said energy beam source is mounted to said support arm for pivotal motion of said energy beam axis about a pivot axis normal to a plane containing said rotation axis and said energy beam axis.

3. The apparatus of claim 1 wherein said support arm is cantilevered from said machine support and has an asymmetrical cross section, said energy beam source being mounted to said support arm at a point remote from said machine support, said adjustable means for adjusting the direction of said energy beam axis comprising pickoff means for detecting rotational position of said support arm, a compensation drive motor, control means for driving said compensation drive motor in response to said pickoff means, and actuator means for adjusting the direction of said energy beam axis in response to said compensation drive motor.

4. The apparatus of claim 3 wherein said actuator means comprises a cam rotatably mounted on said support arm and having a cam surface, said compensation drive motor being connected to rotate said cam, and cam follower means engaged with said cam surface for adjusting direction of said energy beam axis.

5. The apparatus of any one of claims 1 through 4 wherein said adjustable means comprises a cam, cam follower means engaging said cam and connected to adjust direction of said energy beam axis, and means for rotating said cam to shift said cam follower and said energy beam axis.

6. A radio therapy treatment simulator comprising:
   an upstanding machine support,
   a gantry mounted to said machine support for rotation about a substantially horizontal rotation axis,
   a support arm mounted to said gantry and extending along and parallel to said rotation axis, said support arm being subject to different deflections at different positions of rotation of said gantry about said rotation axis,
   an energy beam source mounted on said support arm,
   said energy beam source including means for projecting an energy beam along an energy beam axis tending to nominally intersect said rotation axis at an isocenter point thereon, said energy beam axis being subject to displacement error caused by deflection of said support arm, said energy beam axis being pivotally displaceable about a pivot axis that is substantially perpendicular to said rotation axis and to said energy beam axis and
   compensation means responsive to rotational position of said gantry about said rotation axis for displacing said energy beam axis about said pivot axis in a sense to decrease said error of said energy beam axis in different positions of rotation of said gantry beam.

7. The apparatus of claim 6 wherein said compensation means comprise pickoff means for generating a pickoff signal indicative of rotational position of said gantry, a position compensation motor responsive to said pickoff signal, and means responsive to said motor for displacing said energy beam axis about said pivot axis.

8. The apparatus of claim 7 wherein said compensation means for displacing said energy beam axis comprises a cam connected to be rotated by said compensation motor, and cam follower means engaged with said cam for pivotally displacing said energy beam axis about said pivot axis as said cam rotates.

9. The apparatus of claim 6 wherein said gantry arm is mounted for rotation about said rotation axis for more than 90° of rotation in either direction from a 0° position in which the support arm is substantially directly above the rotation axis, said compensation means including means for pivotally displacing the energy beam axis in one direction when the gantry rotation is less than 90° and in the opposite direction when the gantry rotation is more than 90°.

10. The apparatus of claim 8 wherein said energy beam source includes an energy beam generator mounted on said support arm and a collimator assembly having cross hairs therein, said compensation means for displacing said energy beam axis comprising a pivotal connection between said collimator assembly and said energy beam generator.

11. In radiation therapy apparatus of the type wherein an energy beam generator and collimator assembly are mounted at the end of a support arm that is cantilevered from a gantry, said collimator providing a projected target point adjacent the axis of the energy beam, wherein the gantry is rotatable about a horizontal rotation axis extending substantially parallel to the support arm, and wherein the support arm experiences deflection in an amount that varies in accordance with the angle of rotation of the gantry about the rotation axis, displacing the axis of the beam generated by said energy generator and the target point projected from the collimator assembly, the method of decreasing said target point displacement comprising the steps of pivotally connecting said collimator assembly to said energy beam generator for limited pivotal motion about a pivot axis that is perpendicular to a plane containing said rotation axis and the axis of said energy beam, and pivoting said collimator assembly about said pivot axis by an amount related to the rotational position of said gantry about said rotation axis, in order to shift the axis of said collimator assembly in a sense to decrease the displacement of said beam axis from the isocenter of said gantry.

12. Radiant energy apparatus comprising a patient supporting table, a machine support, an energy beam source including an energy beam generator and a collimator for projecting an energy beam having a beam axis, a support arm mounted to said machine support for rotation about an axis extending through an isocenter point having a predetermined position relative to said machine support, said support arm being subject to different deflections at different positions of rotation about said rotation axis, and said deflections causing displacement of said projected target point from said isocenter point, said support arm extending along and spaced from a portion of said table, pickoff means for detecting rotational position of said support arm, means for mounting said energy beam source to said support arm to enable said energy beam source to project a target point along said beam axis toward said isocenter point, and adjustment means responsive to said pickoff means for effectively adjusting said energy beam source relative to said support arm to decrease said displacement of said projected target point from said isocenter point.

13. The radient energy apparatus of claim 12 wherein said energy beam source and collimator are mounted to said support arm for pivotal motion about a pivot axis normal to a plane containing said rotation axis and said beam axis and wherein said adjustment means comprises means for rotating said energy beam source and collimator about said pivot axis in response to detected rotational position of said support arm.

* * * * *

UNITED STATES PATENT AND TRADEMARK OFFICE
CERTIFICATE OF CORRECTION

PATENT NO. : 4,628,523

DATED : December 9, 1986

INVENTOR(S) : CHESTER L. HEFLIN

It is certified that error appears in the above-identified patent and that said Letters Patent is hereby corrected as shown below:

Please correct face of patent by changing the name of Assignee to OLDELFT CORPORATION OF AMERICA.

Signed and Sealed this

Eighteenth Day of August, 1987

Attest:

DONALD J. QUIGG

Attesting Officer

Commissioner of Patents and Trademarks